US010188361B2

United States Patent
Geiger et al.

(10) Patent No.: US 10,188,361 B2
(45) Date of Patent: Jan. 29, 2019

(54) SYSTEM FOR SYNTHETIC DISPLAY OF MULTI-MODALITY DATA

(71) Applicant: Siemens Healthcare GmbH, Erlangen (DE)

(72) Inventors: Bernhard Geiger, Cranbury, NJ (US); Shaohua Kevin Zhou, Plainsboro, NJ (US); Carol L. Novak, Newtown, PA (US); Daguang Xu, Princeton, NJ (US); David Liu, Richard, TX (US)

(73) Assignee: Siemens Healthcare GmbH, Erlangen (DE)

( * ) Notice: Subject to any disclaimer, the term of this patent is extended or adjusted under 35 U.S.C. 154(b) by 43 days.

(21) Appl. No.: 15/469,878

(22) Filed: Mar. 27, 2017

(65) Prior Publication Data

US 2018/0271460 A1    Sep. 27, 2018

(51) Int. Cl.
*A61B 6/00* (2006.01)
*G01R 33/48* (2006.01)
*G06T 7/00* (2017.01)

(52) U.S. Cl.
CPC ............ *A61B 6/4417* (2013.01); *A61B 6/463* (2013.01); *A61B 6/5235* (2013.01); *A61B 6/5247* (2013.01); *G01R 33/481* (2013.01); *G01R 33/4812* (2013.01); *G01R 33/4814* (2013.01); *G06T 7/0012* (2013.01)

(58) Field of Classification Search
CPC .................. G06F 19/321; G06F 19/00; G06T 2207/30004; G06T 2207/10081; G06T 2207/10072; G06T 2207/10088; G06T 2207/20081; G06T 2207/20101; G06T 2207/20104; G06T 2207/20128; G06T 2207/30008; G06T 2207/30016; G06T 2207/30056; G06T 7/0012; G06T 7/30; G06T 7/12; G06T 7/38; G06T 7/10; G06T 7/11; G06T 7/174; G06T 7/187; G16H 50/20; A61B 6/463; A61B 6/5235; A61B 6/5247; A61B 2090/364; G01R 33/4814; G01R 33/4812; G01R 33/481
See application file for complete search history.

(56) References Cited

U.S. PATENT DOCUMENTS

| 7,590,440 | B2 * | 9/2009 | Lau ................... G06F 17/30265 600/413 |
| 7,751,605 | B2 * | 7/2010 | G ndel ................... A61B 6/032 382/128 |
| 7,899,231 | B2 | 3/2011 | Novak |
| 8,108,024 | B2 * | 1/2012 | Carlsen ..................... G06T 7/30 382/128 |
| 8,363,916 | B2 * | 1/2013 | Assmann ................. G06K 9/34 382/128 |

(Continued)

*Primary Examiner* — Michael Osinski

(57) ABSTRACT

A computer-implemented method for providing a multi-modality visualization of a patient includes receiving one or more image datasets. Each image dataset corresponds to a distinct image modality. The image datasets are segmented into a plurality of anatomical objects. A list of clinical tasks associated with displaying the one or more image datasets are received. A machine learning model is used to determine visualization parameters for each anatomical object based on the list of clinical tasks. Then, a synthetic display of the image datasets is created by presenting each anatomical object according to its corresponding visualization parameters.

11 Claims, 3 Drawing Sheets

(56) References Cited

U.S. PATENT DOCUMENTS

| | | | | |
|---|---|---|---|---|
| 8,384,729 B2* | 2/2013 | Niwa | | A61B 5/0002 345/581 |
| 8,457,710 B2* | 6/2013 | Biglieri | | A61B 5/0555 600/407 |
| 8,565,505 B2* | 10/2013 | Bergmans | | G01R 33/543 378/4 |
| 8,897,532 B2* | 11/2014 | Blaskovics | | A61B 5/055 382/128 |
| 9,542,741 B2* | 1/2017 | Birkbeck | | G06T 7/0012 |
| 9,892,341 B2* | 2/2018 | Reicher | | G06K 9/6267 |
| 10,061,898 B2* | 8/2018 | Wang | | G06F 19/00 |
| 2003/0174872 A1* | 9/2003 | Chalana | | G06K 9/00 382/128 |
| 2003/0228042 A1* | 12/2003 | Sinha | | G06T 7/0012 382/131 |
| 2004/0147840 A1* | 7/2004 | Duggirala | | A61B 8/00 600/437 |
| 2006/0047195 A1* | 3/2006 | Shen | | G16H 50/20 600/407 |
| 2006/0058624 A1* | 3/2006 | Kimura | | A61B 5/055 600/407 |
| 2006/0155577 A1* | 7/2006 | Niemeyer | | G06F 19/321 705/2 |
| 2006/0171578 A1* | 8/2006 | Novak | | G06T 5/50 382/131 |
| 2006/0241408 A1* | 10/2006 | Yakubovsky | | A61B 6/032 600/429 |
| 2006/0251975 A1* | 11/2006 | Taranath | | G06F 19/321 430/7 |
| 2006/0271403 A1* | 11/2006 | Iwasa | | G06Q 10/10 705/2 |
| 2007/0109402 A1* | 5/2007 | Niwa | | A61B 5/0002 348/77 |
| 2007/0127790 A1* | 6/2007 | Lau | | G06F 17/30265 382/128 |
| 2007/0230761 A1* | 10/2007 | Gundel | | A61B 6/032 382/131 |
| 2008/0139921 A1* | 6/2008 | Biglieri | | A61B 5/0555 600/410 |
| 2009/0080779 A1* | 3/2009 | Chefd'hotel | | G06K 9/32 382/209 |
| 2009/0326362 A1* | 12/2009 | Carlse | | A61B 6/037 600/411 |
| 2010/0023556 A1* | 1/2010 | Sawada | | A61B 6/037 707/E17.009 |
| 2010/0061606 A1* | 3/2010 | Geiger | | G06F 19/321 382/128 |
| 2010/0080427 A1* | 4/2010 | Yeluri | | G06F 19/321 382/128 |
| 2010/0091035 A1* | 4/2010 | Kirchberg | | G06K 9/342 345/620 |
| 2011/0206260 A1* | 8/2011 | Bergmans | | G01R 33/543 382/131 |
| 2011/0279477 A1* | 11/2011 | Wang | | G06F 19/321 345/629 |
| 2012/0166211 A1* | 6/2012 | Park | | G06Q 50/22 705/2 |
| 2013/0110548 A1* | 5/2013 | Kutty | | G16H 10/60 705/3 |
| 2013/0129165 A1* | 5/2013 | Dekel | | G06F 19/321 382/128 |
| 2015/0243065 A1* | 8/2015 | Yanagida | | G06F 19/321 345/635 |
| 2015/0261925 A1* | 9/2015 | Wang | | G06F 19/00 705/2 |

\* cited by examiner

SYSTEM FOR SYNTHETIC DISPLAY OF MULTI-MODALITY DATA

TECHNOLOGY FIELD

The present invention relates generally to methods, systems, and apparatuses for providing a synthetic display of multi-modality image data. The technology disclosed here may be used to perform a visualization/rendering of various modalities such as Computed Tomography (CT), Magnetic Resonance Imaging (MRI), Positron Emission Tomography (PET), and Ultrasound data.

BACKGROUND

Medical image modalities such as Computed Tomography (CT), Magnetic Resonance Imaging (MRI), and Ultrasound are capable of providing 3D views of a patient's anatomy. Increasingly, patients are scanned with more than one modality in the course of treatment—such as both CT and MRI—or with more than one sub-type of a modality—such as both T1-weighted and T2-weighted sequences for MRI. Some of the most recently developed medical imaging modalities provide for dual acquisition, such as Dual Energy CT (DECT), Positron Emission Tomography CT (PET-CT) and PET-MR. Even with a single scan acquisition, there can be multiple ways of viewing the data, including with different reconstruction kernels or with different visualization parameters (such as window/level). Physicians need these multiple acquisitions as different clinical tasks are better suited to—or in some cases require—the different modes of imaging. However, reading through all the different acquisitions available for a patient can be time consuming and thus expensive. In today's busy hospital or clinic, physicians need workflow aids that present them the most relevant data in the most efficient manner.

To date, there has been limited work on combining information from different scans for efficient display. In some cases, two types of data are combined with a complete overlay of the two images. The user is responsible for controlling the blend function of how much of the base image is shown versus how much of the overlaid image. Similarly all medical imaging workstations allow the user to do manual control of window/level.

SUMMARY

Embodiments of the present invention address and overcome one or more of the above shortcomings and drawbacks, by providing methods, systems, and apparatuses that incorporate different types of multi-modality data into a synthetic patient display that presents the most relevant and necessary clinical information to the physician. As described in further detail below, a machine learning-based approach is used to learn over time correlations between clinical tasks and optimal presentation of imaging data. Thus, integrated displays can be generated automatically or semi-automatically to present multi-modality imaging data in an optimal manner for a given set of tasks.

According to some embodiments, a computer-implemented method for providing a multi-modality visualization of a patient includes receiving one or more image datasets. Each image dataset corresponds to a distinct image modality. The image datasets are segmented into a plurality of anatomical objects. A list of clinical tasks associated with displaying the one or more image datasets are received. A machine learning model is used to determine visualization parameters for each anatomical object based on the list of clinical tasks. Then, a synthetic display of the image datasets is created by presenting each anatomical object according to its corresponding visualization parameters. For example, if the visualization parameters correspond to colors, each anatomical object may be presented according to a distinct color.

In some embodiments, the aforementioned method further includes identifying abnormalities in the anatomical objects depicted in the image datasets. The machine learning model may then use the abnormalities to determine the visualization parameters. The machine learning model may be trained offline by analyzing past radiology reports to determine correspondences between past clinical tasks performed by users and image modalities used to perform those past clinical tasks.

Users can provide input in different embodiments to interact with the synthetic display or the underlying data. For example, in some embodiments, the aforementioned method further includes receiving a user selection of a particular image modality and modifying the synthetic display to present each anatomical object using the particular image modality. This user selection may be made via graphical user interface component that allows a user to select between a plurality of views such as modality specific views (presenting all anatomical objects in a particular image modality) and a blended view that presents anatomical objects in a mix of two or more image modalities. In some embodiments, user input is received associating the anatomical object with a particular image modality. Based on this input, the synthetic display can be updated so that each anatomical object is displayed according to the modality associated with the object. In some embodiments, the method further includes detecting one or more changes to the synthetic display made by a user. Based on these changes and the list of clinical tasks, the machine learning model can be updated A computer-implemented method for providing a multi-modality visualization of a patient includes analyzing one or more past radiology reports to determine correspondences between past clinical tasks performed by users and image modalities used to perform those past clinical tasks. A machine learning model is trained based on the correspondences between past clinical tasks performed by users and image modalities used to perform those past clinical tasks. Next, one or more image datasets are received, with each image dataset corresponding to a distinct image modality. The machine learning model may then be used to create a synthetic display of a plurality of anatomical objects in the image dataset suitable for performing one or more selected tasks. This synthetic display presents the anatomical objects using two or more imaging modalities.

A system for providing a multi-modality visualization of a patient comprising a monitor and a parallel processing platform. The parallel processing platform is configured to train a machine learning model based on the correspondences between past clinical tasks performed by users and image modalities used to perform those past clinical tasks. The platform receives one or more image datasets and user selected tasks. Each image dataset corresponding to a distinct image modality and comprising a plurality of anatomical objects. The platform then uses the machine learning model to generate a set of visualization parameters for each anatomical object suitable for performing the user selected tasks. A synthetic display of the anatomical objects may then be created on the display, presenting each anatomical object according to its corresponding set of visualization parameters.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses related to the synthetic display of multi-modality data using a technique referred to herein as intelligent General Organ Recombination, or "iGOR." iGOR takes multiple medical imaging datasets (such as CT and MR) of a given patient as input, and combines them into a visualized output; the specific output is based on predefined clinical tasks such as liver cancer evaluation, lung cancer screening, cardiac screening, etc.

Figure 1:
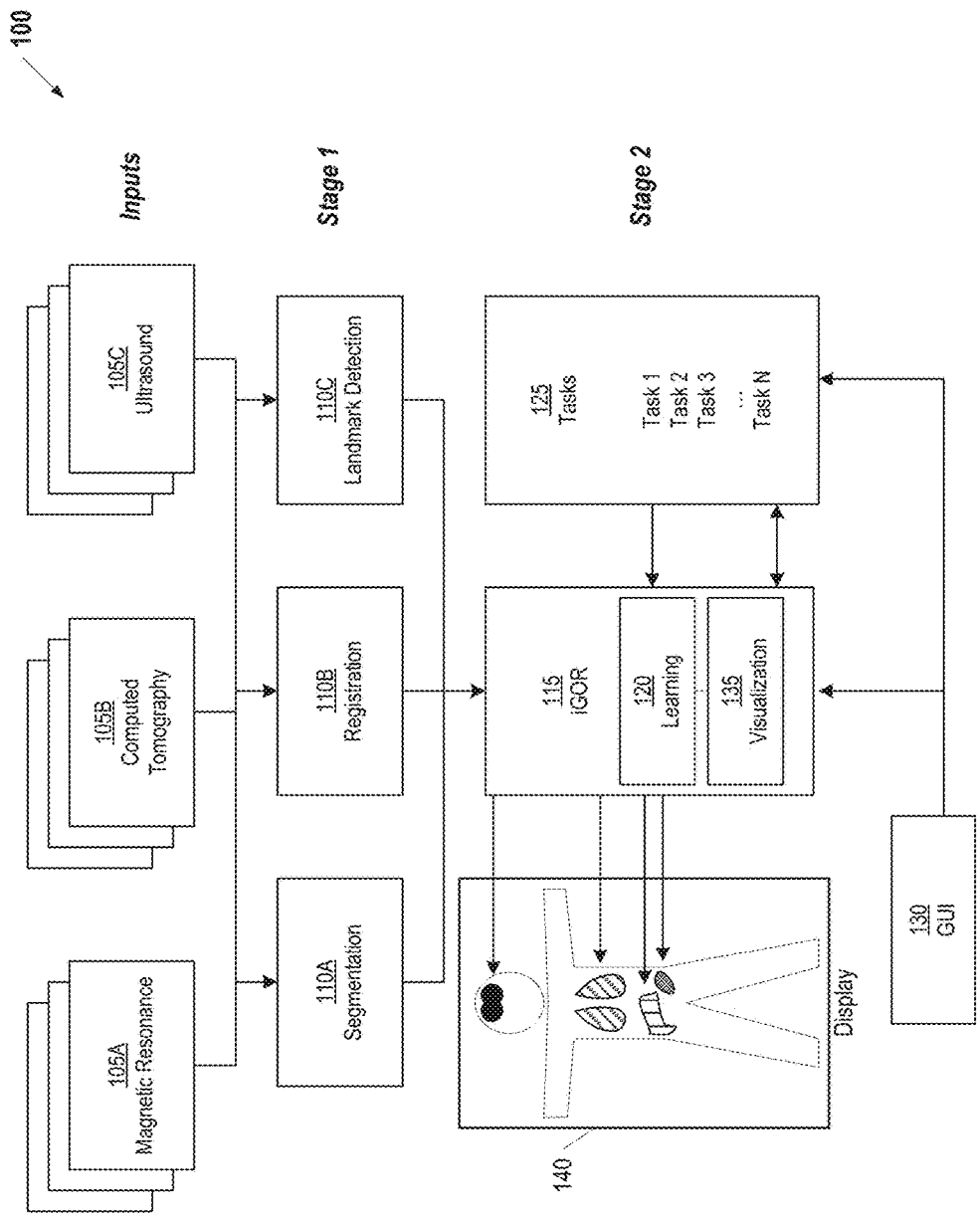
FIG. 1 illustrates an example system which uses iGOR (intelligent General Organ Recombination) to combine multiple input medical datasets and produce an efficient visualization for clinicians, according to some embodiments.

FIG. 1 illustrates an example system 100 which uses iGOR to combine multiple input medical datasets and produce an efficient visualization for clinicians, according to some embodiments. Briefly, the process is partitioned into two stages. In the first stage, datasets from multiple modalities are automatically registered, landmarks (or abnormalities) are automatically detected, and the organs are automatically segmented. In the second stage, a learning algorithm is used to select the optimal way to combine and present the information to accomplish different clinical tasks. The resulting image can recombine the organs from different imaging modalities to show, for example, the lungs as they look in CT, with the liver as it looks in MR and the spleen as it looks in Ultrasound. The combined image is then presented on Display 140. This Display 140 could be a computer monitor or other equivalent device (e.g., smartphone or tablet screen). It should be noted that for the purposes of the present description, FIG. 1 presents the Display 140 as black and white; however, in practice, the Display 140 would utilize color to present a clearer and more obvious indication of the differences being observed.

The inputs to the system 100 include a plurality of MR Images 105A, a plurality of CT Images 105B, and a plurality of Ultrasound Images 105C. These image datasets can be received by the system 100, for example, by interacting with one or more medical imaging scanners or extracting the image datasets from a database of pre-generated images. In one embodiment, the image datasets can be received by the system 100 via user input (e.g., uploading via GUI).

As shown in FIG. 1, the first stage of the system contains modules for Segmentation 110A, Registration 110B, and Landmark Detection 110C. These modules 110A, 110B, and 110C automatically register the different input images with each other, automatically detect anatomic landmarks within the images, and automatically segment the boundaries of the organs. In general, any technique known in the art can be used for implementing the modules and each module can be fully automated or may include some manual input. Additionally, the order of application of the modules may be defined to facilitate efficient processing of the images. For example, Landmark Detection 110C can be performed first, either automatically or via a user selection of anatomical landmarks or other landmark points on each image. Then, Registration 110B can be performed based on the landmarks. Similarly, Segmentation 110A may be performed based on the landmarks, and possibly on the Registration 110B information as well.

It should be noted that the modules 110A, 110B, and 110C shown in the first stage of FIG. 1 are exemplary and additional or alternate modules may be used in different embodiments to provide different functionality. For example, in one embodiment, the landmark detection module is replaced or augmented with automated detection of abnormalities such as lung nodules or liver lesions. In still another embodiment, the registration matrix is the identity matrix because the different modalities are acquired simultaneously, as is the case for some types of DECT, PET-CT and PET-MR.

The input images processed at stage 1 may also include functional images which are derived from original images. These functional images may include, for example, iodine maps or perfusion maps from DECT. However, functional images can also comprise feature maps or probability maps derived from machine learning classifiers. This allows relevant information to be presented to the user when the derived images contain information about cancer likelihood or other biomarkers. The method presented here allows a probability map of, for example, liver cancer to be shown at the same time as a probability map for lung cancer in a single volume, even when the probability maps are obtained by different functions.

In the second stage of the system shown in FIG. 1, different Clinical Tasks 125 (i.e., Task1 through Task N) are selected as desired by the user through a user interface (UI) 130. Example tasks include liver cancer evaluation, lung cancer screening, cardiac screening, etc. In an alternate embodiment, the clinical task is selected automatically based on landmarks and/or abnormalities detected in Stage 1. For example, a system to automatically detect lung nodules may be included in stage 1. If lung nodules are detected that are clinically relevant (based on size and other features), this triggers the lung screening task to be selected.

Based on the clinical task that was selected—either by the user or automatically triggered—the input datasets that were registered, segmented and detected in stage 1 are combined and presented to the clinician to support the particular clinical task using iGOR 115. As shown in FIG. 1, iGOR 115 includes a Learning Module 120 and a Visualization Module 135. The Learning Module 120 learns the parameter selection to combine and visualize the data according to training examples. The Visualization Module 135 uses parameters provided by the Learning Module 120 to interface with the display computing devices in order to provide the optimal display for the task.

Various types of learning may be applied by the Learning Module 120. For example, in some embodiments, the Learning Module is a neural network that uses the tasks and the results of the Stage 1 modules 110A, 110B, and 110C as inputs. Based on these inputs, the visualization parameters are determined. Deep learning or other more complex models could be used in some embodiments to provide additional learning functionality to the Learning Module 120.

In some embodiments, the Learning Module 120 can operate in two modes. One mode is offline. In the offline mode, the Learning Module 120 analyzes all user interactions and data inputs from a large set of training data. This training data may include, for example, radiology reports; these reports are automatically analyzed to detect what clinical task has been executed and what image modalities were used to perform that task. As an example, a radiology report may state that T1-weighted MR images were read and that the liver was examined for the presence of metastases. This serves as an example input that T1-weighted MR is an effective modality for looking at the liver if metastases are a possibility. Yet another report may state that sharp kernel CT was used to examine the lungs for possible lung nodules. This, in turn, serves as an example input that sharp kernel CT is a good modality for lung cancer screening. Training of the Learning Module 120 may be performed across multiple clinical locations to provide a robust database for training. For example, training from multiple hospitals may be aggregated and used for training purposes. Alternatively, data from a single clinical location may be used for training to allow the Learning Module 120 to accurately reflect the visualization preferences of that particular location. Moreover, in some embodiments, the Learning Module 120 associates user identifiers (e.g., name, employee ID, etc.) with each task during learning to allow iGOR 115 to customize visualizations to particular users.

Given a sufficiently large set of example data from radiology reports, the Learning Module 120 identifies coherent patterns of preferred imaging modalities for specific clinical tasks. The automatic data registration and segmentation computations in stage 1 are used to present to the user a single image that shows—for example—the liver from the MR image at the same time as the lungs from the CT image. Each region can be displayed by the Visualization Module 135 (described below) with different parameters (e.g., window/level, color maps, etc.). In another example, bones can be removed or enhanced on MR data based on segmentation masks from CT data.

In other embodiments of the invention, the Learning Module 120 in stage 2 operates in an online model, during which it does continuous learning and updates the learned setting as the system progressively collects more data from each new radiology report. In this way, the Learning Module 120 can learn hospital-specific preferences after being deployed.

The Visualization Module 135 uses the visualization parameters developed by the Learning Module 120 and uses it to present the image data on a Display 140. This presentation of image data is referred to herein as a "synthetic display" because it may combine the image data in a manner that is not a direct representation of a single image acquisition. The Visualization Module 135 may be configured with the physical specifications of the Display 140, such as the screen size, aspect ratio, resolution, color space, color depth, refresh rate, and interfaces. If the physical specifications support the visualization parameters provided by the Learning Module 120, then the Visualization Module 135 may simply format the images and present them on the Display 140. However, if the Display 140 does not support all of the specified visualization parameters, the Visualization Module 135 may adjust the parameters based on the specifications of the Display 140. For example, if the visualization parameters specify that liver images should be depicted in a particular color that is not available on the Display 140, the Visualization Module 135 may use the color space and/or color depth specification values to select an alternative color that approximates the requested color.

In some embodiments, a Graphical User Interface (GUI) 130 allows the clinician to select between the different visualization methods provided by iGOR 115. In the example above with both MR and CT, the user may use a slider or other interface component to select between a pure MR view, a pure CT view, and a blended view of the different organs. Alternatively, the user may use radio buttons or other interface components to select which organs should be visualized in MR and which in CT. Visualization can also be selected based on specific rules, such as "show all areas where MR is hyper dense and CT signal is above 100 HU."

In some embodiments, iGOR 115 can be further adapted to support multi-phase image visualization techniques, such as for medical imaging as may be utilized in hepatic perfusion visualization. Techniques for multi-phase image visualization are discussed in U.S. Pat. No. 8,755,635 to Geiger et al., issued Jun. 17, 2014, entitled "Method and system for data dependent multi phase visualization," the entirety of which is incorporated herein by reference.

Figure 2:
FIG. 2 shows an example synthetic display showing the recombination of two different CT visualization settings following segmentation of the lung region in stage 1.

FIG. 2 shows an example synthetic display showing the recombination of two different CT visualization settings following segmentation of the lung region in stage 1. The task-specific setting allows simultaneous examination of the lungs for possible nodules, and examination of the chest region for other abnormalities.

Figure 3:
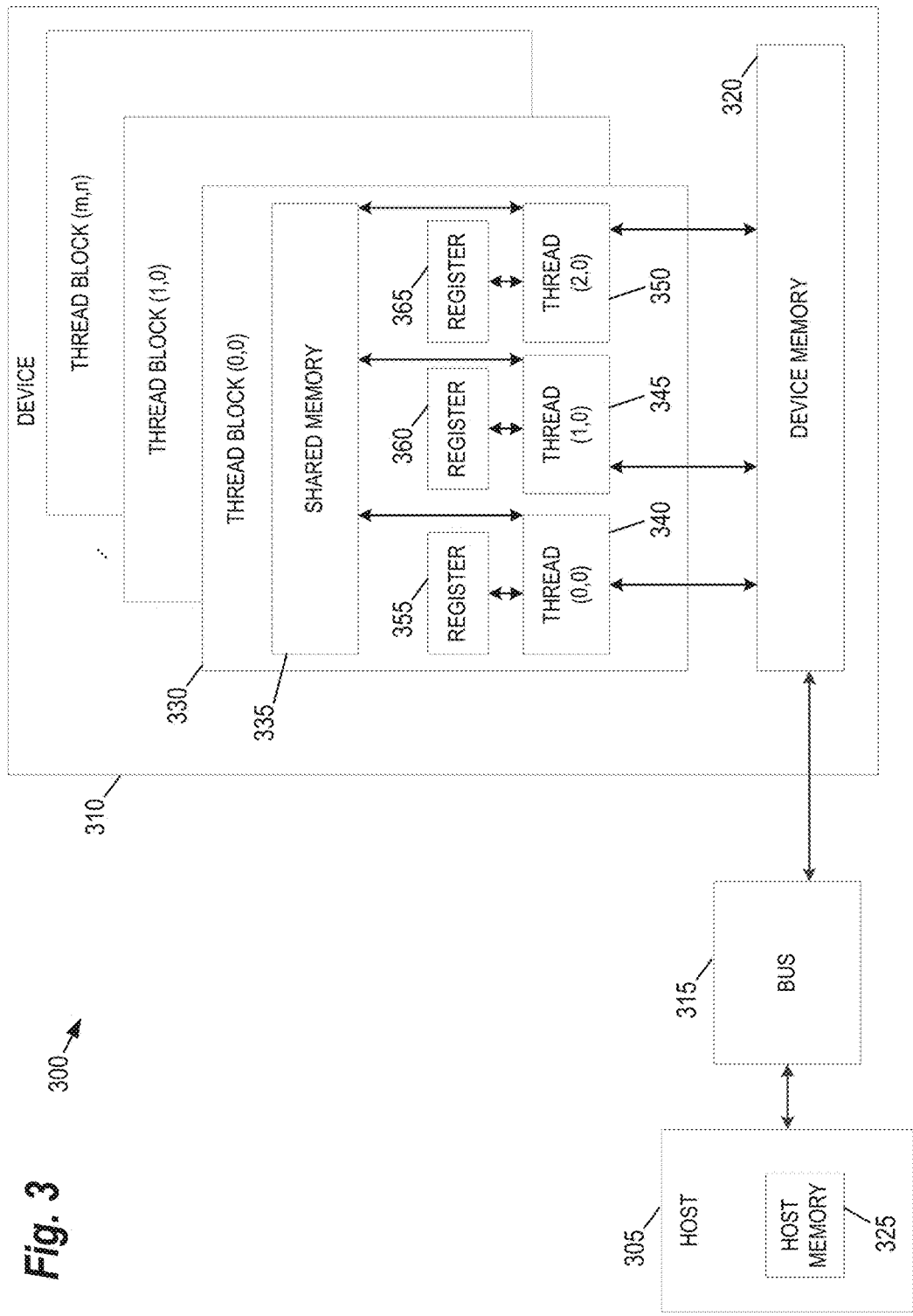
FIG. 3 provides an example of a parallel processing memory architecture that may be utilized to perform computations related to learning and visualization operations performed by iGOR, according to some embodiments of the present invention.

FIG. 3 provides an example of a parallel processing platform 300 that may be utilized to perform computations related to learning and visualization operations performed by iGOR, according to some embodiments of the present invention. This platform 300 may be used in embodiments of the present invention where NVIDIA™ CUDA (or a similar parallel computing platform) is used. The architecture includes a host computing unit ("host") 305 and a graphics processing unit (GPU) device ("device") 310 connected via a bus 315 (e.g., a PCIe bus). The host 305 includes the central processing unit, or "CPU" (not shown in FIG. 3), and host memory 325 accessible to the CPU. The device 310 includes the graphics processing unit (GPU) and its associated memory 320, referred to herein as device memory. The device memory 320 may include various types of memory, each optimized for different memory usages. For example, in some embodiments, the device memory includes global memory, constant memory, and texture memory. The GUI 130 shown in FIG. 1 may interface with this parallel processing platform 300, either via a direct connection or via one or more computer networks.

Parallel portions of a deep learning application may be executed on the platform 300 as "device kernels" or simply "kernels." A kernel comprises parameterized code configured to perform a particular function. The parallel computing platform is configured to execute these kernels in an optimal manner across the platform 300 based on parameters, settings, and other selections provided by the user. Additionally, in some embodiments, the parallel computing platform may include additional functionalities to allow for automatic processing of kernels in an optimal manner with minimal user inputs.

The processing required for each kernel is performed by grid of thread blocks (described in greater detail below). Using concurrent kernel execution, streams, and synchronization with lightweight events, the platform 300 of FIG. 3 (or similar architectures) may be used to parallelize training of a neural network such as the one applied by Learning Module 120.

The device 310 includes one or more thread blocks 330 which represent the computation unit of the device 310. The term thread block refers to a group of threads that can cooperate via shared memory and synchronize their execution to coordinate memory accesses. For example, in FIG. 3, threads 340, 345 and 350 operate in thread block 330 and access shared memory 335. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 3, the thread blocks 330 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints. To address this limitation, learning operations may be configured in various manners to optimize use of the parallel computing platform. For example, in some embodiments, the operations of the Learning Module 120 may be partitioned such that multiple kernels evaluate different tasks (e.g., Tasks 125) simultaneously in view of the available image data provided in Stage 1 (see FIG. 1). Alternatively, different input images could be evaluated in parallel across the entire task list.

Continuing with reference to FIG. 3, registers 355, 360, and 365 represent the fast memory available to thread block 330. Each register is only accessible by a single thread. Thus, for example, register 355 may only be accessed by thread 340. Conversely, shared memory is allocated per thread block, so all threads in the block have access to the same shared memory. Thus, shared memory 335 is designed to be accessed, in parallel, by each thread 340, 345, and 350 in thread block 330. Threads can access data in shared memory 335 loaded from device memory 320 by other threads within the same thread block (e.g., thread block 330). The device memory 320 is accessed by all blocks of the grid and may be implemented using, for example, Dynamic Random-Access Memory (DRAM).

Each thread can have one or more levels of memory access. For example, in the platform 300 of FIG. 3, each thread may have three levels of memory access. First, each thread 340, 345, 350, can read and write to its corresponding registers 355, 360, and 365. Registers provide the fastest memory access to threads because there are no synchronization issues and the register is generally located close to a multiprocessor executing the thread. Second, each thread 340, 345, 350 in thread block 330, may read and write data to the shared memory 335 corresponding to that block 330. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 310 to read and/or write to the device memory. Device memory requires the longest time to access because access must be synchronized across the thread blocks operating on the device. For example, in some embodiments, the processing of each image or task at Stage 2 (see FIG. 1) is coded such that it primarily utilizes registers and shared memory and only utilizes device memory as necessary to move data in and out of a thread block.

The embodiments of the present disclosure may be implemented with any combination of hardware and software. For example, aside from parallel processing architecture presented in FIG. 3, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A GUI, as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A computer-implemented method for providing a multi-modality visualization of a patient, the method comprising:
   receiving one or more image datasets, each image dataset corresponding to a distinct image modality;
   segmenting the one or more image datasets into a plurality of anatomical objects;
   receiving a list of clinical tasks associated with displaying the one or more image datasets;
   for each anatomical object, using a machine learning model to determine visualization parameters for the anatomical object based on the list of clinical tasks; and
   creating a synthetic display of the one or more image datasets by presenting each anatomical object according to its corresponding visualization parameters.

2. The method of claim 1, further comprising:
   identifying one or more landmarks in the one or more image datasets; and
   performing registration of the one or more image datasets to yield registered image data, wherein the machine learning model uses the one or more of (i) the landmarks and (ii) the registered image data to determine the visualization parameters.

3. The method of claim 2, wherein the registered image data comprises an identity matrix.

4. The method of claim 1, further comprising:
   identifying abnormalities in the plurality of anatomical objects depicted in the one or more image datasets,
   wherein the machine learning model uses the abnormalities to determine the visualization parameters.

5. The method of claim 1, wherein the visualization parameters correspond to colors and each anatomical object is presented in the synthetic display according to a distinct color.

6. The method of claim 1, further comprising:
   receiving a user selection of a particular image modality; and
   modifying the synthetic display of the one or more image datasets to present each anatomical object using the particular image modality.

7. The method of claim 6, wherein the user selection is made via graphical user interface component that allows a user to select between a plurality of views comprising:
   a plurality of modality specific views, each modality specific view presenting all anatomical objects in a particular image modality, and
   a blended view that presents anatomical objects in a mix of two or more image modalities.

8. The method of claim 1, further comprising:
   for each anatomical object, receiving user input associating the anatomical object with a particular image modality; and
   presenting each anatomical object in the synthetic display according to the image modality associated with the anatomical object.

9. The method of claim 1, wherein the machine learning model is trained offline by analyzing one or more past radiology reports to determine correspondences between past clinical tasks performed by users and image modalities used to perform those past clinical tasks.

10. The method of claim 1, further comprising:
    after creating the synthetic display, detecting one or more changes to the synthetic display made by a user; and
    updating the machine learning model based on the one or more changes and the list of clinical tasks.

11. A system for providing a multi-modality visualization of a patient, the system comprising:
    a monitor; and
    a parallel processing platform configured to:
      train a machine learning model based on the correspondences between past clinical tasks performed by users and image modalities used to perform those past clinical tasks;
      receive one or more image datasets, each image dataset corresponding to a distinct image modality and comprising a plurality of anatomical objects;
      receiving one or more user selected tasks;
      use the machine learning model to generate a set of visualization parameters for each anatomical object suitable for performing the one or more user selected tasks; and
      create a synthetic display of the plurality of anatomical objects on the display, wherein the synthetic display presents the anatomical object according to its corresponding set of visualization parameters.

* * * * *